United States Patent [19]

Nanaumi

[11] Patent Number: 4,653,495
[45] Date of Patent: Mar. 31, 1987

[54] LASER MEDICAL APPARATUS

[75] Inventor: Yasuaki Nanaumi, Kuroiso, Japan

[73] Assignee: Kabushiki Kaisha Toshiba, Kawasaki, Japan

[21] Appl. No.: 867,581

[22] Filed: May 27, 1986

Related U.S. Application Data

[63] Continuation of Ser. No. 690,121, Jan. 10, 1985, abandoned.

[30] Foreign Application Priority Data

Jan. 13, 1984 [JP] Japan .................................. 59-4380

[51] Int. Cl.$^4$ ............................................. A61B 17/00
[52] U.S. Cl. ................................ 128/303.1; 128/355; 128/398
[58] Field of Search ........ 128/303.1, 303.12, 397–401, 128/395, 362, 633, 634, 355; 330/96.24

[56] References Cited

U.S. PATENT DOCUMENTS

| | | | |
|---|---|---|---|
| 1,751,584 | 3/1930 | Hansell | 128/398 |
| 3,188,188 | 6/1965 | Norton | 350/96.24 |
| 3,204,326 | 9/1965 | Granitsas | 350/96.24 |
| 4,060,724 | 11/1977 | Heine et al. | 128/398 |
| 4,461,294 | 7/1984 | Baron | 128/395 |

FOREIGN PATENT DOCUMENTS

| | | | |
|---|---|---|---|
| 31073 | 7/1981 | European Pat. Off. | 128/303.1 |
| 2717421 | 11/1978 | Fed. Rep. of Germany | 128/303.1 |

OTHER PUBLICATIONS

"Dermatologic Laser Treatment Successfully Completed in Japan" by Ohshiro, Laser & Electro Optik No. 3, vol. 9, Sep. 1977, pp. 34–35.
"Excimer Laser Surgery of the Cornea" by Trokel et al. Amer. J. Opth., vol. 96, No. 6, pp. 710–715.
"Fiber Bundle Scanner for Laser Coagulation Treatment" by Fujii et al. Optics & Laser Technology, Feb. 1982, pp. 39–40.

Primary Examiner—Kyle L. Howell
Assistant Examiner—David Shay
Attorney, Agent, or Firm—Finnegan, Henderson, Farabow, Garrett & Dunner

[57] ABSTRACT

The invention is primarily intended to provide a laser medical apparatus which radiates a patient's diseased spot with laser beams issued from a source and introduced from the distal end face of an optical fiber unit through a hand piece set at the output side. The invention thus provides a laser medical apparatus characterized in that the optical fiber unit comprises a large number of fibers each having a polygonal section. A protective board prepared from a laser-permeable material is detachably fitted to the laser output end face of the hand piece and laser beams issued from the source with a prescribed distribution of energy intensities are conducted through the optical fiber unit composed of fibers having a polygonal section for equalizing the energy intensity distribution laser beams are radiated over a broad area without irregularities and medical treatment can be undertaken uniformly in a short time. The protective board detachably fitted to the hand piece enables laser beams to be radiated with the hand piece in contact with the patient's diseased spot, so the hand piece can be accurately held during the medical operation and an efficacious medical treatment is ensured.

6 Claims, 15 Drawing Figures

FIG. 2(a)
(PRIOR ART)
FIG. 2(b)
(PRIOR ART)
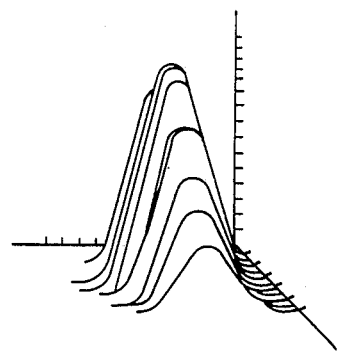
FIG. 3(a)
(PRIOR ART)
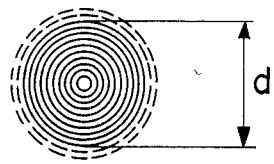
FIG. 3(b)
(PRIOR ART)
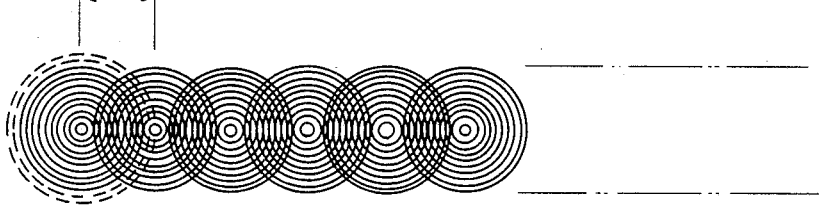
FIG. 3(c)
(PRIOR ART)
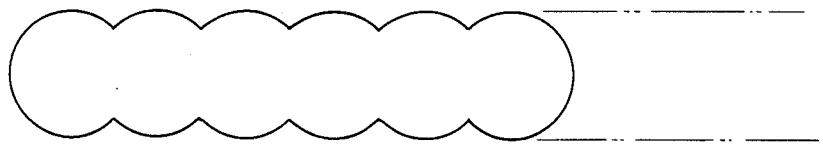

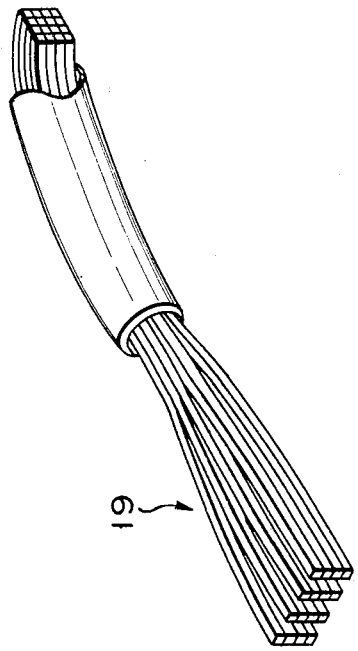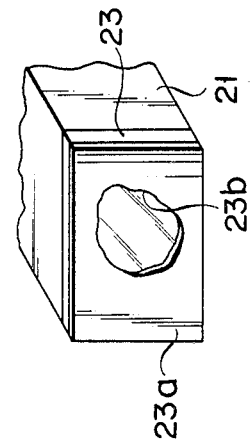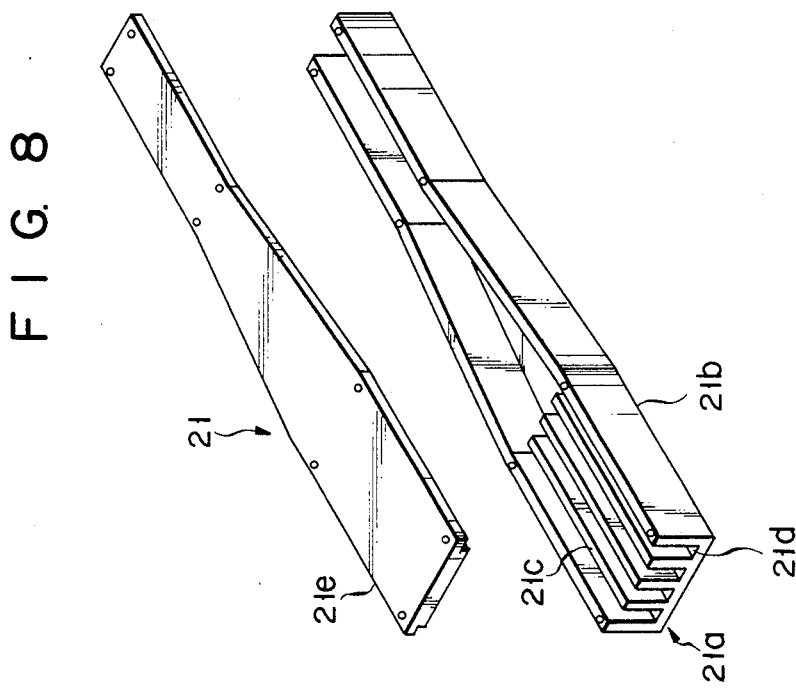

LASER MEDICAL APPARATUS

This application is a continuation of application Ser. No. 690,121, filed Jan. 10, 1985, now abandoned.

BACKGROUND OF THE INVENTION

This invention relates to a laser medical apparatus used, for example, in plastic surgery or dermatology, and, more particularly, to a laser medical apparatus which is adapted for the eradication or medical treatment of pigmented naevi consisting of abnormal blood vessel or pigmented cell agglomerations by radiating laser beams having a proper amount of energy onto said agglomerations.

Hitherto, various medical treatments of naevi have been attempted in the fields of surgery, dermatology and radiopathology. Namely, surgical medical treatment such as excision, suture, skin grafting and surface skin exfoliation. In dermatology, pharmacotherapy, dry ice and electrolysis treatment are used. Radiotherapy involves the application of radium, cobalt, strontium, etc. The above-listed processes may be considered the main types of medical treatment. However, these treatments have the drawback that despite the major invasion of the body a satisfactory therapeutic effect cannot be obtained. Moreover, surgical treatment is painful and sometimes requires long hospitalization. Consequently, a strong demand has been made for the improvement of the treatment.

In recent years, histological research has been conducted on naevi and the origin of the naevi is being studied, but progress is slow. Abnormal pigmented cells observed in, for example, the so-called vascular naevus are generally less transparent than normal cells, and absorb visible light rays more strongly than the normal transparent cells. Therefore, visible high energy light rays radiated on said abnormal cells are selectively absorbed, and changed into heat energy. As a result, the abnormal cells are broken down due to intense burning. Conversely, the normal cells have higher transparency and absorb little of the above-mentioned high energy light rays, resulting in less heat damage. Consequently, the radiation of the aforementioned high energy light rays on the pigmented naevi causes only the abnormal cells to be selectively burnt off. In this case, the more transparent normal cells, perspiratory glands and tissue absorb little light, and are not irreversibly damaged. Therefore, the burnt normal cells and tissue are rapidly healed with only minute cicatrices remaining. If, therefore, it is possible to select such visible light wavelengths whose light energy is absorbed less by the normal cells of the naevi of the diseased spot and is absorbed to a greater extent by the pigmented cells, and if it is possible to set the energy density of said wavelengths at a prescribed level, then the pigmented cells can be selectively destroyed. Laser beams are light rays which satisfy the above-mentioned requirements.

At present, various laser medical apparatuses have been proposed. FIG. 1 denotes one type of such an apparatus. Reference numeral 1 denotes an apparatus body. The body 1 comprises a power source 1A, laser oscillator 1B and operation panel 1C. Laser beams issued from the laser oscillator 1B are conducted through an optical fiber 3 and ejected from the distal end of a hand piece 4. Argon laser rays, which have a typical wavelength of 5,140 Å, and ruby laser rays, which have a typical wavelength of 6,943 Å, provide a relatively large output of a visible light range effective for the treatment of pigmented naevi and are now being used in practical applications. The ruby laser beams can provide high light energies and a broad radiation area, but have the drawback that the ruby laser beams are issued by pulse oscillation and require a longer overall radiation time, thereby lengthening the treatment period. Conversely, the argon laser beams have the drawback that they provide a lower light output (about several watts) than the ruby laser beams, but have the merit that they can be better controlled and are radiated on a relatively small area. Moreover, they can be operated and handled at a higher speed and are more adapted for the treatment of a delicate structures.

The above-mentioned laser medical apparatus is generally used by holding the hand piece 4. While the operator observes the diseased spot, the spot on which the laser beams are to be radiated is progressively shifted by an extent corresponding to the flux of the laser beams radiated from the end of the hand piece 4. The operator carries out treatment by radiating laser beams intermittently or continuously using a pedal switch, for example.

However, in the laser flux issued from the laser oscillator, the energy intensity progressively decreases from the center to the peripheral portion as seen from FIG. 2. This is called Gauss' distribution. FIG. 2a indicates Gauss' distribution by planar contour lines. FIG. 2b is a 3-dimensional view of Gauss' distribution.

When laser beams which have different energy intensities are radiated on a patient's diseased spot, radiation irregularities arise in accordance with the different energy intensities as typically set forth in FIG. 3a. It is therefore necessary to apply such an amount of laser beams as can heal the patient's diseased spot without causing ugly cicatrices or scars to be left at the central portion of said diseased spot in which the highest laser beam energies tend to concentrate. The requisite conditions by which the laser beam energy should be determined are being clarified from animal tests and clinical experience. At present, it is possible to determine the types of patient reaction to laser beams, and the extent of the cicatrices remaining, according to the magnitude of the laser output and the volume of its flux (that is, the area of laser radiation). Further, it is possible to determine the efficiency of radiant heat and propagated heat by measuring the laser beam radiation time, and also to define the moisture quantity in the case of thermal treatment and the cooling effect of blood by measuring the intervals at which laser beams are radiated.

FIG. 3b illustrates the case where a plurality of linearly arranged laser beam fluxes having a radiation diameter d are ejected under uniform conditions. It has been determined from clinical experience that the purpose can be attained if the pitch P between the respective laser beam fluxes, that is, the overlapping rate thereof, corresponds to 30 to 40% of the radiation diameter d. FIG. 3c shows the condition of a diseased spot which has been subjected to the radiation of laser beams and which has been healed after a certain lapse of time without any marks or cicatrices.

Description will be given with reference to FIG. 4a of the process of radiating laser beams on a patient's diseased spot. A plurality of laser fluxes linearly arranged in a partially superposed fashion are radiated. Thereafter, a similar group of laser fluxes are radiated near the above-mentioned laser fluxes at an interval $d_1$, which is smaller than the radiated diameter d of said laser fluxes. This second laser flux-radiated spot is referred to as "D₁". Namely, the radiation of laser fluxes is carried out in a zebrine pattern. This zebrine pattern laser flux-radiating process is deemed the best method whose efficacy has been proved by experiments undertaken in regards to the effect of radiated heat and propagated heat and the cooling effect of the blood. FIG. 4b shows the patient's diseased spots which were subjected to the above-mentioned zebrine pattern laser flux-radiating process, and which resulted in the healed conditions D', D'₁ after the lapse of a certain length of time.

FIG. 5a illustrates laser fluxes applied to the non-radiated intervening section of the zebrine pattern laser flux-radiating process of FIG. 4b. FIG. 5b indicates the patient's diseased spots which were healed after a lapse of a certain length of time by the application of the zebrine pattern laser flux-radiating process on the intervening spaces shown in FIG. 4a.

An actual medical operation with the above-mentioned laser apparatus is carried out in the following manner. The operator grips the hand piece 4, and moves the wrist to set the hand piece 4 perpendicular to the surface of the diseased spot. The operator holds the hand piece 4 in such a manner that the output end face is at a prescribed distance from the diseased spot. While observing that portion of the diseased spot which is to be subjected to laser beams, the operator linearly moves the hand piece 4 to an extent corresponding to the total length of the plurality of laser fluxes linearly issued from the hand piece 4 in succession and in a partially superposed fashion. The medical treatment is performed by continuously or intermittently radiating laser beams by actuating a pedal switch, for example. The reason why the hand piece 4 is spaced away from the patient's diseased spot at a certain distance is to prevent the laser beam output from being reduced or the end face of the hand piece fiber from being contaminated due to the blood or flesh particles splattering from the diseased or applicated spot onto said fiber end face during the laser treatment.

However, the surface of the diseased spot and the distal end of the hand piece 4 are not generally brought into contact with each other. Therefore, it requires considerable skill to securely hold the hand piece 4 perpendicularly to the diseased spot and at a prescribed distance. Further, tremendous difficulties are encountered in uniformly arranging with the naked eye the circles of the radiated laser fluxes (generally having a diameter of about 2 mm) or preserving a prescribed interval between the respective radiation circles of partially superposed laser fluxes arranged in the zebrine pattern (i.e., an interval between the centers of the circles). If, therefore, the arrangement of the circular radiated laser fluxes is rendered irregular, and the respective radiated laser fluxes are superposed on each other to an excessive extent, the diseased spot may be excessively destroyed, resulting in cicatrices, which harmfully affects the laser treatment. If the respective groups of the radiated circular laser fluxes are spaced from each other too broadly, the intervening regions will remain untreated. If it is impossible to preserve the prescribed energy density of radiated laser fluxes (a product of the radiation time and the distance between the respective circles of radiated laser fluxes, assuming that the laser output remains constant), then the respective laser fluxes tend to produce burn marks. Laser fluxes having a greater energy density than is required for the temperature rise of the abnormal cells of the diseased spot are particularly likely to indiscriminately heat the surrounding non-diseased cells which require no laser treatment, thereby destroying normal cells.

As mentioned above, the conventional laser medical apparatus used in plastic surgery or dermatology has various drawbacks. When applied to actual medical treatment, the practicality of the conventional laser apparatus is reduced, if the diseased spot is too broad. If the treatment continues for a long time, the operator will tire and the patient must maintain a certain posture for a long time without moving. Also, considerable difficulties are encountered in carrying out an effective laser treatment and the operator must use great skill.

SUMMARY OF THE INVENTION

This invention has been accomplished in view of the above-mentioned circumstances. Accordingly, the invention is primarily intended to provide a laser medical apparatus which radiates a patient's diseased spot with laser beams issued from a source and introduced from the distal end face of an optical fiber unit through a hand piece set at the output side. To attain the above-mentioned object, this invention provides a laser medical apparatus characterized in that the optical fiber unit comprises a large number of fibers having a polygonal section. A protective board prepared from a laser-permeable material is detachably fitted to the laser output end face of the hand piece. Laser beams issued from the source with a prescribed distribution of energy intensities are conducted through the optical fiber unit composed of fibers having a polygonal section for equalizing the energy intensity distribution. Laser beams are radiated over a broad area without irregularities and medical treatment can be undertaken uniformly in a short time. The protective board detachably fitted to the hand piece enables laser beams to be radiated with the hand piece in contact with the patient's diseased spot so the hand piece can be accurately held during the medical operation and an efficacious medical treatment is ensured.

BRIEF DESCRIPTION OF THE DRAWINGS

FIG. 2(a) indicates the Gauss' distribution of laser beams by planar contour lines;

FIG. 2(b) is a 3-dimensional view of this Gauss' distribution;

FIGS. 3(a) to 3(c) are plan views of examples of radiation of laser beams issued from a conventional laser medical apparatus, indicating the pattern of laser beam fluxes and the healed condition;

FIG. 6a is an oblique view of a modification of a protective board involved in the laser medical apparatus of FIG. 6;

FIG. 8 is an oblique view of a square fiber arrangement and a hand piece shape.

DETAILED DESCRIPTION OF THE PREFERRED EMBODIMENTS

Figure 1:
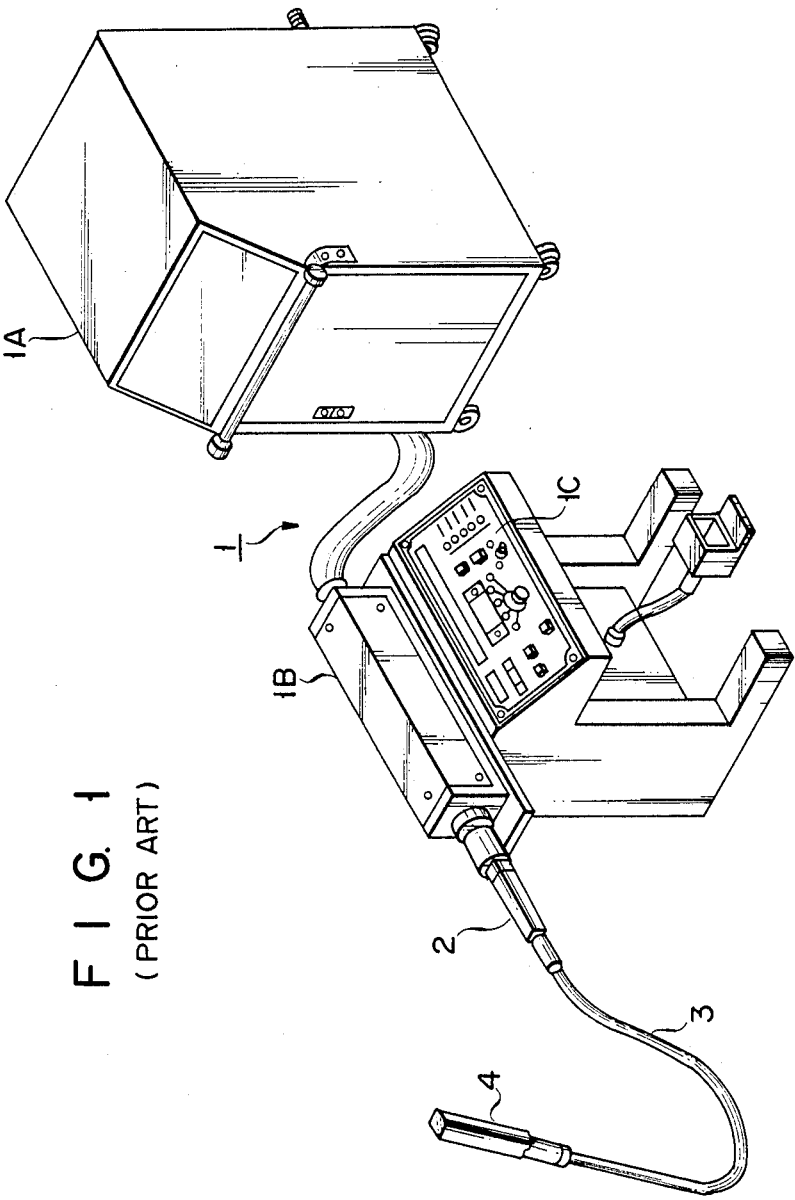
FIG. 1 is a schematic oblique view of a conventional laser medical apparatus.
Figure 4A:
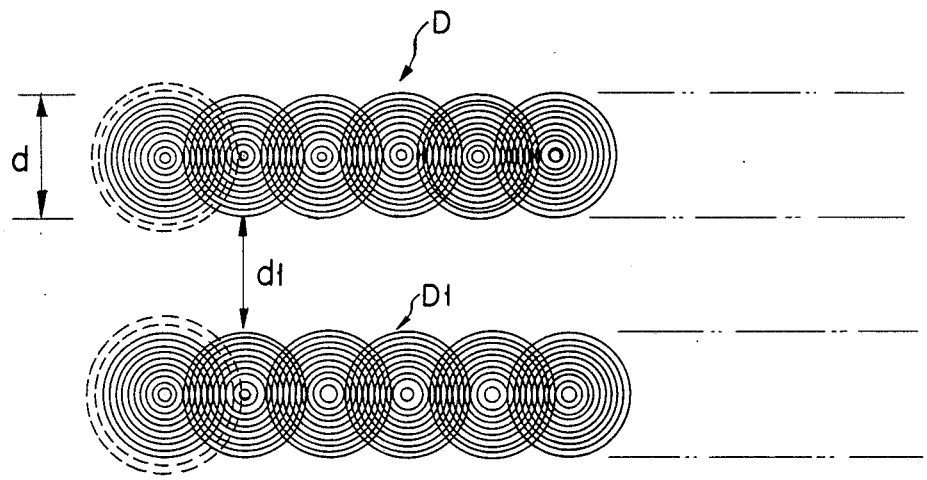
FIGS. 4(a) and 4(b) are plan views of examples of radiation of laser beam fluxes issued from a conventional laser medical apparatus in the zebrine pattern, showing the healed conditions.
Figure 4B:
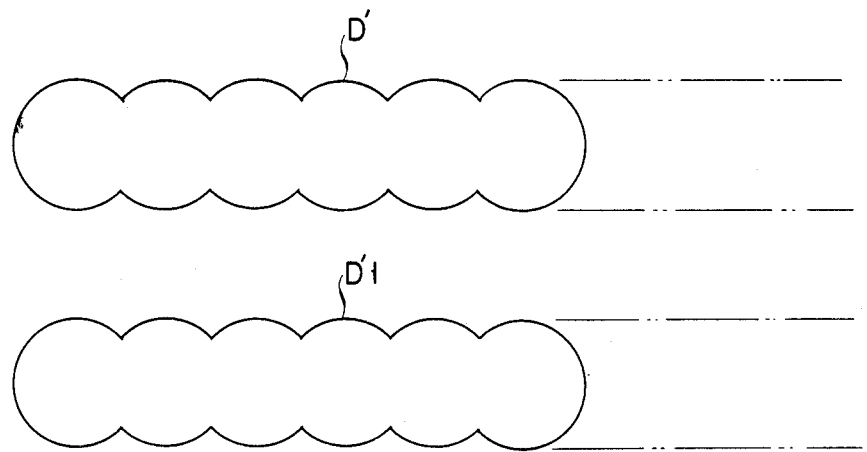
Figure 5A:
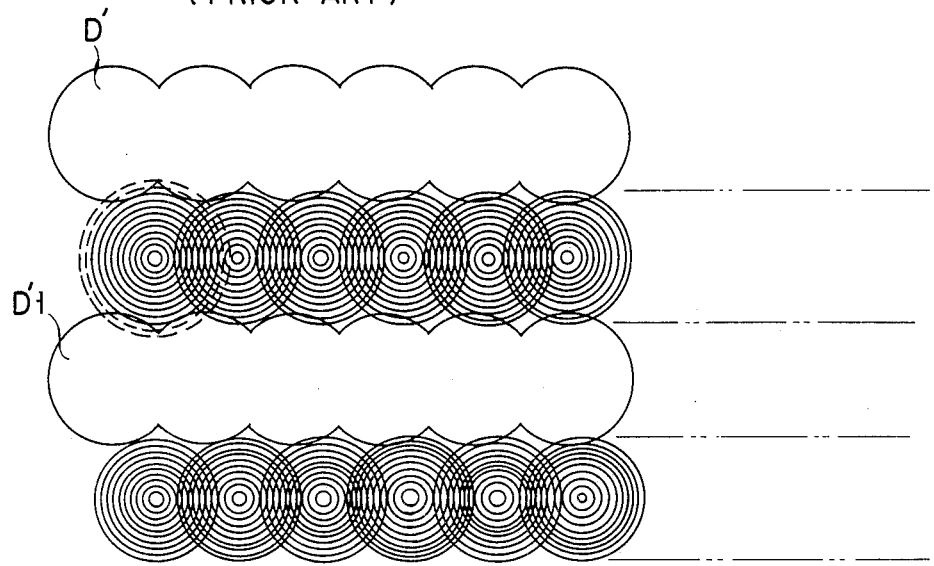
FIGS. 5(a) and 5(b) are a plan view of an example of radiation of laser beam fluxes issued in the zebrine pattern so as to fill up the interstices of the preceding zebrine pattern laser beam fluxes, and a plan view showing the healed condition of the whole diseased spot, respectively.
Figure 5B:
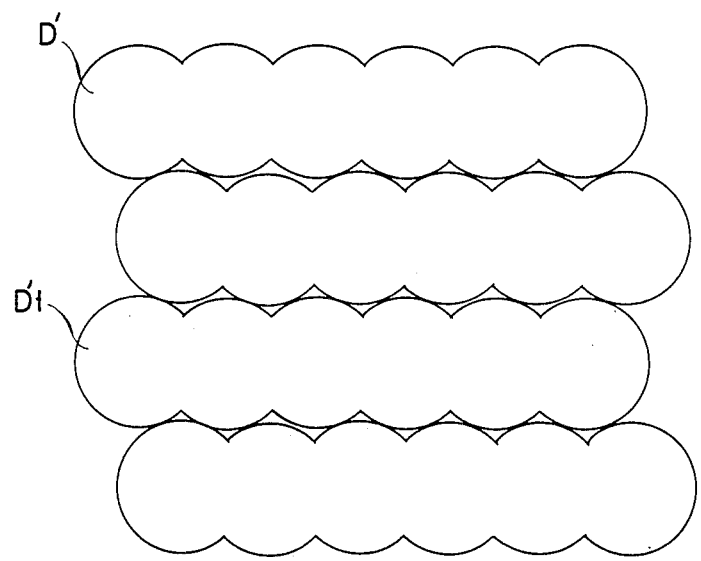
Figure 6:
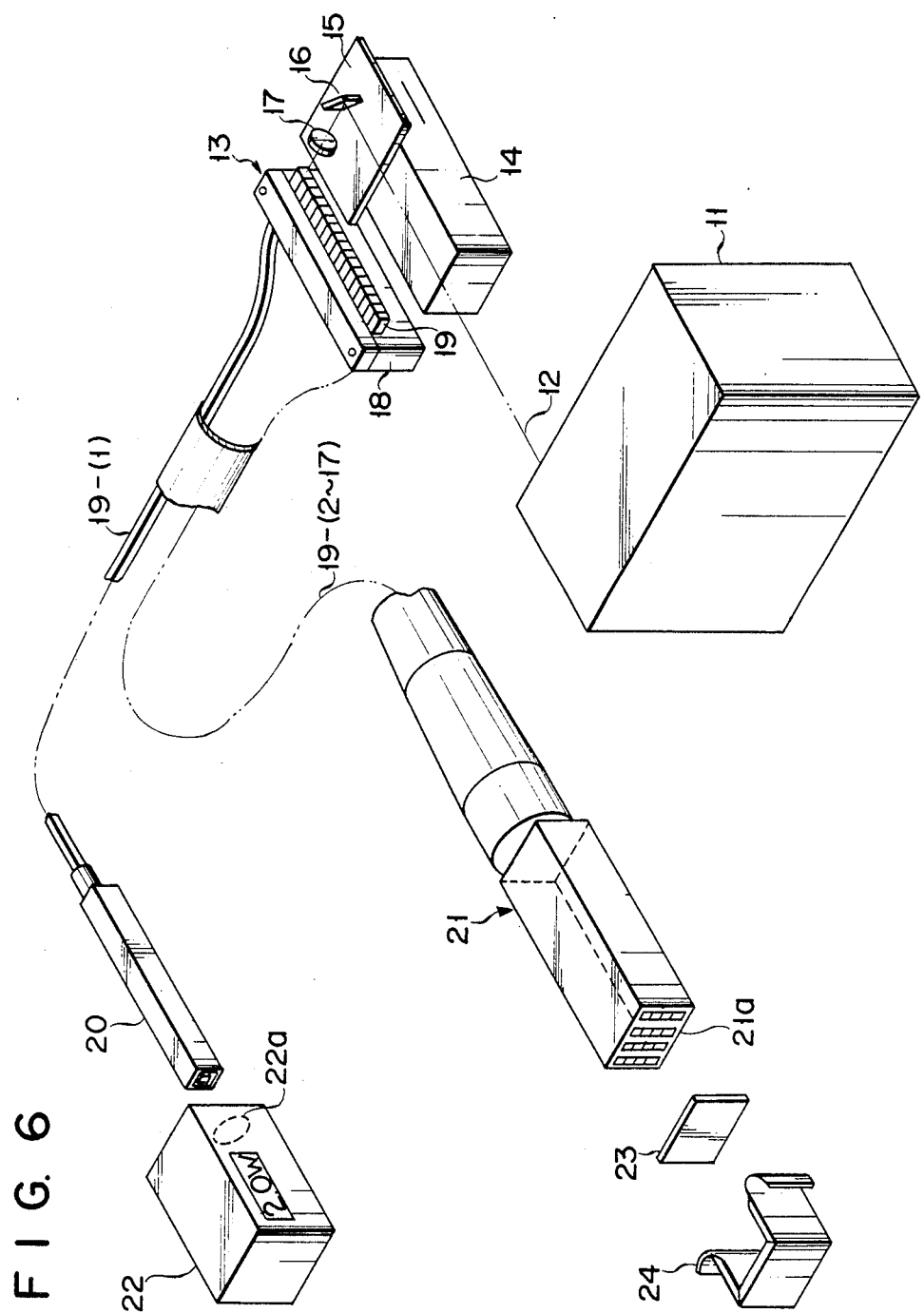
FIG. 6 is a schematic, exploded, oblique view of a laser medical apparatus embodying this invention.
Figure 7:
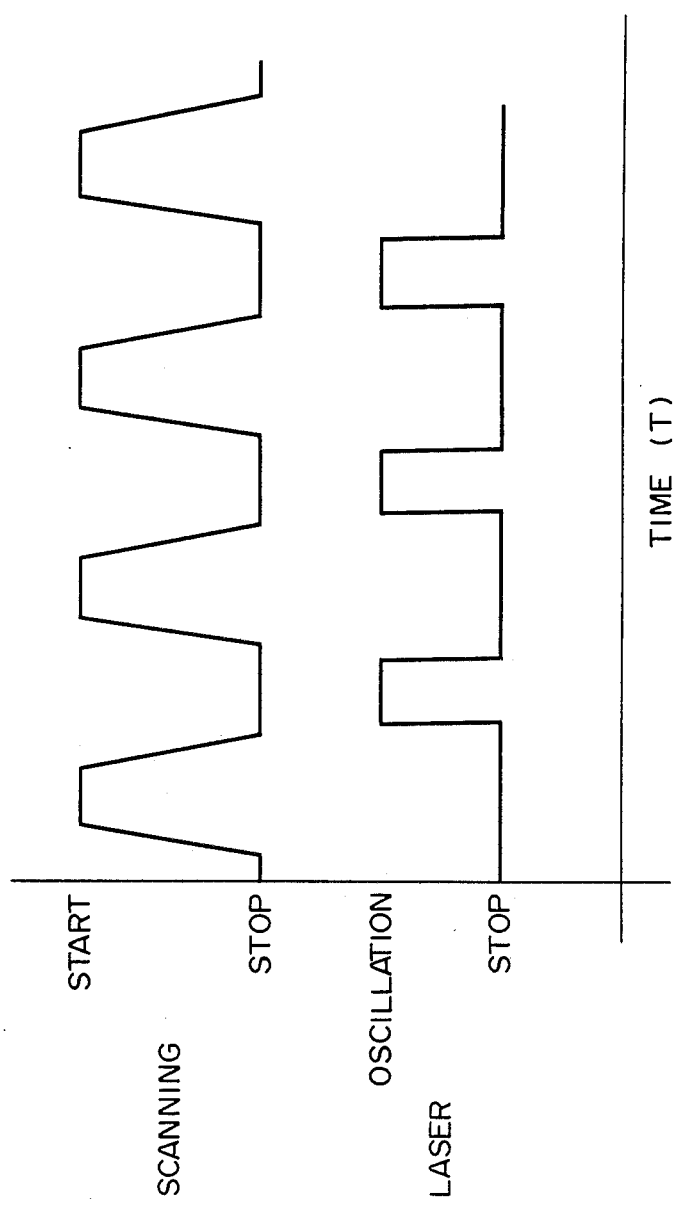
FIG. 7 illustrates the timing in which laser beams are issued and that in which the patient's diseased spot is scanned by said laser beams.

FIG. 6 is a schematic, exploded, oblique view of a laser medical apparatus embodying this invention. A reference numeral 11 denotes a laser oscillator. A laser beam 12 issued from said oscillator 11 has its course bent in a perpendicular direction by a mirror 16 provided in a known laser beam scanning unit 13 which is reciprocated in the direction of the optical axis of the laser beam. The laser beams thus bent are focused by a lens 17 provided in said laser beam scanning unit 13. The flux of focused laser beams is conducted to the input end face of the respective fibers 19 which have a square section are arranged in the prescribed positions so as to cause the axis of the fibers to be set in parallel with the optical axis of the lens 17. The laser beam scanning unit 13 generally comprises a drive section 14 and scanning section 15. The aforementioned mirror 16 and lens 17 are mounted on said scanning section 15. Scanning by the scanning section 15 and the issue of a laser beam are synchronized in the manner shown in FIG. 7. The laser beam 12 is issued when scanning is brought to an end, that is, at the set position of the optical fiber 19 having a square section (hereinafter simply referred to as "a square optical fiber"). The issued laser beam enters the input end face of said square optical fiber 19.

The laser beam input end faces of a plurality of (for example, 17) square optical fibers 19 are linearly fixed on a fiber holder 18 at a pitch corresponding to the extent to which the scanning is progressively shifted along said fiber holder 18. The square optical fibers 19 are bundled together after leaving the laser beam input end faces. The output sections of the square optical fibers 19 are securely held together in a hand piece 21.

The hand piece 21 is constructed as shown in the oblique view of FIG. 8 by providing a plurality of linearly extending projections 21c in the hand piece body 21b. The output end sections of the plural flexible square optical fibers 19 capable of freely conducting incoming laser beams and ensuring the uniform distribution of the laser beam intensity are inserted into the grooves 21d defined between said projections 21c. The square optical fibers 19 are securely set in place by a cover plate 21e in such a manner that the end faces of the respective square optical fibers 19 are aligned across the opening of the hand piece body 21b.

A protective board 23 prepared from a laser beam-permeable material, for example, transparent acrylic resin is detachably fitted by means of a keeper plate 24 to the laser beam output side 21a of the hand piece 21 in order to avoid the deposition of tissue or materials splattering from the skin of the diseased spot at the time of medical treatment onto the output end faces of the square optical fibers 19.

Further, among a plurality of square optical fibers 19, at least one 19-(1), for example, the first optical fiber counted from the right side (FIG. 6), is separated from the other square optical fibers 19 and brought into a single optical fiber hand piece 20 instead of being conducted to the hand piece 21. Consequently, hand piece 21 is hereinafter referred to as "a multi hand piece".

Description will now be given of a laser medical apparatus embodying this invention. The operator selects the single hand piece 20 or multi hand piece 21 in consideration of the size and shape of the diseased section requiring the laser treatment. The electric switch of an operation section (not shown) is set at the single or multi mode as occasion demands. In the single mode, the laser beam scanning unit 13 does not drive the scanning section 15, which is actuated in the multi mode. In the initial stage of operation, the scanning section 15 occupies the original position, namely, it is situated at the position of the first square optical fiber 19-(1). In the single mode, therefore, the scanning section 15 is set at this position to carry out the oscillation of laser beams. Namely, a single hand piece 20 will suffice. In the single mode, the laser beams that are actually output can be measured by inserting the hand piece 20 into the hole in the light-receiving section of, for example, an output meter. Or it is possible to ensure a better medical effect by a trial clinical radiation of laser beams to observe the actual condition of medical treatment and correct the laser beam output to a proper level. Where a small diseased spot is treated in the single mode, the laser beam output side of the hand piece 20 is fitted with a protective board (not shown) as in the case of the multi hand piece 21.

The multi mode medical treatment is carried out in the following manner after taking the above-mentioned preparatory step. The operator grips the hand piece 21, attaches the end face protective board 23 and its keeper plate 24 to the prescribed position at the distal end of the hand piece 21 and brings the hand piece 21 into contact with the diseased spot of the patient while observing the spot. A scanning-start signal is issued to the laser beam scanning unit 13 by actuating a pedal switch, for example. At this time, scanning and laser oscillation are carried out at the same time, and laser beams are successively supplied to the input end face of the square optical fibers 19. The laser beams conducted through the square optical fibers 19 are issued at the output end face thereof after repeating full reflections at the inner surrounding walls, thereby ensuring the uniform distribution of laser beam energy. The laser beams permeating the transparent protective cover 23 are radiated onto the diseased spot. Therefore, the diseased spot, even if large, can be medically treated by laser beams without leaving burnt cicatrices. Since the hand piece 21 can be attached to the diseased spot, the positioning and holding of the hand piece 21 is facilitated. Furthermore, even if the patient happens to move, the prescribed diseased spot can be treated easily and reliably. A broad diseased spot is medically treated by successively changing the position of the hand piece 21.

According to this invention, a plurality of laser beam-conducting optical fibers having a square section are received in the hand piece 21. The laser beam output side of the hand piece 21 is fitted with a detachable protective board prepared from a laser beam-permeable material. Even if the hand piece is attached to the diseased spot, the blood and flesh particles scattered from the diseased spot will settle only on the protective board, thereby enabling the continuation of medical treatment simply by exchanging the soiled protective board for a fresh one. Being able to attach the hand piece 21 to the diseased spot facilitates accurate positioning and holding. The use of optical fibers each having a square section for successive scanning enables a series of radiation patterns corresponding to the shape of the square section to be formed, and ensures the uniform distribution of the optical energy of laser beams while they are conducted through these optical fibers. The scanning of the diseased spot by laser beams radiated through said optical fibers can ensure uniform and efficient medical treatment of a large diseased spot in a shorter time than was possible with the conventional laser medical apparatus.

Figure 9:
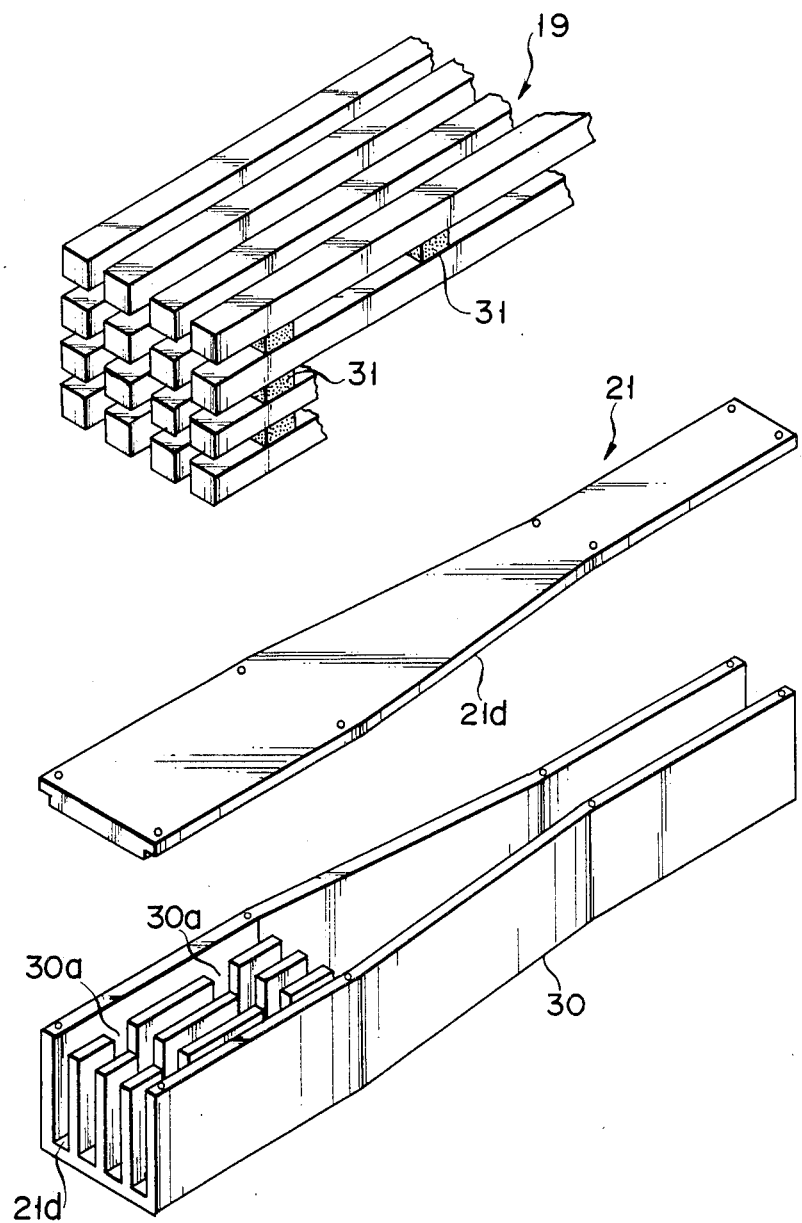
FIG. 9 is an oblique view of a square fiber arrangement and a modified hand piece shape.

This invention is not limited to the foregoing embodiment, but can be modified in various ways without departing from the object of the invention. The above-mentioned embodiment involves the hand piece body 21b comprising square optical fibers 19 arranged in a matrix form of 4 by 4, as illustrated in FIGS. 6 and 8. As shown in the oblique view of FIG. 9, however, it is possible to construct a hand piece body 30 by providing not only four linearly extending grooves 21d, but also grooves 30a in the projections 21c (shown in FIG. 8), which perpendicularly intersect the linearly extending grooves 21d, and inserting spacers 31 in said grooves 30a, thereby arranging the square optical fibers 19 in such a manner that they are spaced from each other lengthwise and crosswise. Thus, the square optical fibers 19 can be arranged in various patterns in the hand piece body 30, thereby changing the shape of the laser beam radiation field. Obviously, the square optical fibers 19 can be held close together in the hand piece body 30 instead of the above-mentioned separated state in order to vary the laser beam radiation field as the need arises.

The laser beam radiation field can be changed not only by the above-mentioned variation of the arrangement of the square optical fibers, but also by the change of the sequence in which the square optical fibers are radiated, namely by the change of the positional order of the square optical fibers on the input side of the scanning unit and/or output side of the hand piece. Further, the laser beam-permeable protective board 23 shown in FIG. 6a may be replaced by a laser beam-impermeable protective masking board 23a, and the desired laser beam radiation field can be provided by cutting out a hole 23b in said masking board 23a corresponding to the shape of the diseased spot undergoing the radiation of laser beams.

The optical fiber 19 need not have a square section but may have a triangular or polygonal section. The number of the optical fibers 19 may be varied to match the designed arrangement pattern, insofar as their flexibility is not impaired.

As described above, the present invention offers the advantages that the insertion of a plurality of laser beam conductive polygonal optical fibers ensures the unification of the laser beam intensity distribution in the hand piece body and provides uniform laser beam radiation of not only the individual optical fibers but also of the whole group. The output end faces of the plural optical fibers are arranged in a pattern matching the condition of the diseased spot, thereby realizing an efficient laser beam radiation and efficacious medical treatment. The laser beam radiation through a plurality of optical fibers is mechanically carried out in proper sequence by the single positioning of the hand piece, ensuring a correct laser beam radiation. The substantial contact of the laser beam output distal end of the hand piece with the diseased spot makes possible the radiation of laser beams through a plurality of optical fibers by a single scanning process and facilitates the positioning of the hand piece in the succeeding laser beam radiation. The single positioning of the hand piece can radiate laser beams over a broader field than has been possible with the conventional laser beam medical apparatus, thereby dispensing with the need for great operator skill and saving the patient from having to remain stationary for a long time. Thus, a laser medical apparatus which has a uniform laser beam output and which is easy to operate is provided.

What is claimed is:

1. A laser medical apparatus, comprising:
    a laser beam source for issuing a laser beam;
    an optical fiber unit having a plurality of optical fibers each having polygonal cross section, the optical fibers having input end faces through which the laser beam from the source is introduced into the optical fibers and output distal ends through which the laser beam is issued from the optical fibers;
    a hand piece provided at the output distal ends of the optical fibers, the hand piece having therein a plurality of linear, opaque spaced-apart projections, said projections defining therebetween a plurality of linear first grooves of rectangular cross section extending longitudinally with respect to said hand piece with said optical fibers being inserted within said first grooves to terminate in a laser beam output end face; and
    a protective board formed of a laser beam permeable material, which is detachably provided on the laser beam output end face of the hand piece, thereby radiating the laser beam from the output distal ends to a patient through the hand piece and the protective board.

2. The laser medical apparatus according to claim 1 wherein said projections have side walls forming said grooves, said side walls having therein second grooves intersecting perpendicularly said first grooves and spacers inserted in said second grooves to maintain said optical fibers spaced-apart within said first grooves.

3. The laser medical apparatus according to claim 1, wherein said optical fibers intended for the conduction of laser beams have a rectangular cross section.

4. The laser medical apparatus according to claim 1, wherein said protective board is provided with a laser beam-permeable pattern forming a radiation field of the laser beams which matches the shape of the patient's diseased spot.

5. The laser medical apparatus according to claim 4, wherein said laser beam-permeable pattern is formed by using a protective board with a laser beam-impermeable masking material and providing a cutout portion which matches the shape of the patient's diseased spot.

6. The laser medical apparatus according to claim 1, wherein at least one of said plural optical fibers is branched off from the group to be connected to a different hand piece.

* * * * *